United States Patent [19]

Ibbott

[11] Patent Number: 4,619,252

[45] Date of Patent: Oct. 28, 1986

[54] THERAPEUTIC METHOD AND THERAPEUTIC MEANS USING A SHEETLIKE BATTERY

[76] Inventor: Jack K. Ibbott, 17-7, Nishiazabu 4-chome, Minato-ku, Tokyo 106, Japan

[21] Appl. No.: 683,462

[22] PCT Filed: Apr. 16, 1984

[86] PCT No.: PCT/JP84/00193

§ 371 Date: Dec. 13, 1984

§ 102(e) Date: Dec. 13, 1984

[87] PCT Pub. No.: WO84/04045

PCT Pub. Date: Oct. 25, 1984

[30] Foreign Application Priority Data

Apr. 15, 1983 [JP] Japan .................................. 58-65624
Feb. 8, 1984 [JP] Japan .................................. 59-20101

[51] Int. Cl.$^4$ .............................................. A61N 1/24
[52] U.S. Cl. ..................... 128/82.1; 128/362; 604/20
[58] Field of Search ....................... 128/82.1, 362, 390, 128/379–382, 391, 419 R, 783, 798, 802; 429/94, 118, 127, 145, 247; 604/20

[56] References Cited

U.S. PATENT DOCUMENTS

| 1,032,324 | 7/1972 | Breakfield | 128/391 |
| 4,142,521 | 3/1979 | Konikoff | 128/82.1 |
| 4,474,570 | 10/1984 | Ariura et al. | 128/798 |

FOREIGN PATENT DOCUMENTS 1020740 12/1957 Fed. Rep. of Germany ...... 128/379

Primary Examiner—William E. Kamm
Attorney, Agent, or Firm—Wenderoth, Lind & Ponack

[57] ABSTRACT

A therapeutic method includes placing a sheetlike battery with a negative electrode thereof in contact with an affected part and attaching the battery to the skin by a covering member which covers the positive electrode of the battery. A therapeutic device is formed by the sheetlike battery and covering member which has an area larger than the battery and which is attached to the positive electrode side of the battery. The covering member is attached to the skin at the peripheral portion thereof after placing the negative electrode side of the battery in contact with an affected part of a human body.

27 Claims, 8 Drawing Figures

THERAPEUTIC METHOD AND THERAPEUTIC MEANS USING A SHEETLIKE BATTERY

BACKGROUND OF THE INVENTION

The present invention relates to a therapeutic method and therapeutic means for curing an affected part by applying a voltage to the human body.

Heretofore, it has been known that a voltage applied to a certain part of the human body stimulates the muscle in that part, activating the flow of the body fluids. On basis of this principle, there have been proposed several therapeutic apparatuses for applying a high voltage to the human body.

An example of such an apparatus is constructed such that a pair of positive and negative electrodes are arranged to interpose an affected part therebetween and applied with a comparatively high voltage. This type of apparatus, however, is dangerous unless it is used in a correct manner. Moreover, the apparatus itself is relatively large in size, so that the therapy cannot be performed except during a special treatment time at rest, because the electrodes have to be attached to the affected part.

This invention has been made in order to overcome the above-mentioned disadvantages. Accordingly, it is an object of this invention to provide a therapeutic method and therapeutic means for curing an affected part by using a sheetlike battery that generates a voltage low enough not to endanger the human body.

SUMMARY OF THE INVENTION

The present inventor has developed a sheetlike battery as disclosed in the specification of PCT/JP84/00100 (corresponding to U.S. patent application Ser. No. 675,060, filed Dec. 7, 1984) and, during the investigation of various applications of this sheetlike battery, has accomplished the present invention.

That is, the present invention was accomplished on the basis of the finding of the present inventor that the sheetlike battery produces a remarkable therapeutic effect when the negative electrode side of the battery is placed in contact with an effected part of a body and attached thereto by an adhesive tape or the like.

According to the therapeutic method of the present invention, the negative electrode of the sheetlike battery is placed in contact with an affected part, and the battery is attached to the skin with a covering member such as film that covers the positive electrode of the battery, thereby causing an electric current to flow from the positive electrode side to negative electrode side through the affected skin part.

The reasons why the above-mentioned therapeutic method achieves the therapeutic effects can be considered from various experiments of the present inventor, as follows:

(1) First, it is considered that when an electric energy flows through the human body, some kinds of disease germs and bacteria are killed or the activities thereof are suppressed.

That is, in the event that the negative electrode side of the sheetlike battery was attached onto an itchy erythema of athlete's foot by an adhesive tape, the itchiness was removed almost immediately. And, when the battery was removed after one day, the erythema has disappeared and did not appear again thereafter. It is assumed from this fact that the electric energy flowed through the erythema and killed the bacteria in that part.

(2) It is also considered that the body fluids and self-curing ingredients therein flow along with the movement of the electric energy and are absorbed into the body part to which the negative electrode of the battery abuts, so that skin diseases and the like at said body part are cured.

In the experiments conducted by the present inventor, it was observed that when the sheetlike battery is kept in contact with the affected part of the skin, a large amount of moisture (sweat) oozes out of the affected part. It is considered from this fact that the body fluids move along the flow of the electric energy and ooze out at the body part contacting the negative electrode of the sheetlike battery. As is well known, body fluids contain some ingredients which cure a wound and the like by themselves, so that it is considered that these ingredients are also drawn, like the above-mentioned moisture, to the body part contacting the negative electrode of the battery to promote curing. In other experiments, where the sheetlike battery was attached to a very dry part of the skin, such a change was observed that the part of the skin contacting the battery became moist after several minutes. This means that moisture in the tissue of the human body is drawn to the skin surface. In view of the fact that the body moisture permeates through the part where the battery is attached, it can be considered that the self-curing ingredients naturally existing in the body will also be drawn to the battery contacting part together with the moisture, whereby the skin disease, wound or the like is cured rapidly.

(3) It is considered that the therapeutic effect of the battery is caused by the increase of minus (−) ions at the body part contacting the negative electrode of the battery, as the electric energy generated by the battery flows through the human body.

That is, these minus (−) ions are effective for the human body, and it is known that by increasing the amount of minus ion, the therapeutic effect such as killing of bacteria, sanitary effects such as deodorizing, and many other healthful effects can be obtained. Namely, when the materials, such as various liquid ingredients (mineral etc.) in the human body, exist in the liquid state, these materials are equiliberated in the form of plus ions and minus ions in the liquid. When an electric current, however small it may be, flows through such ionized materials, the plus ions and minus ions are attracted to the respective points where the plus and minus are applied in the current and highly concentrated at these points. Accordingly, it can be considered that when the above described sheetlike battery is attached in such a manner that the negative electrode side comes into contact with the human body, due to the small electric current caused by such attachment of the battery, minus ions in the body fluids are drawn through the tissues of the body to the part where the negative electrode of the battery contacts and are concentrated thereat, whereby the skin disease or the like at the body part is cured.

The above and other objects of the present invention as well as the features thereof will be described in more detail with reference to the accompanying drawings.

Figure 1:
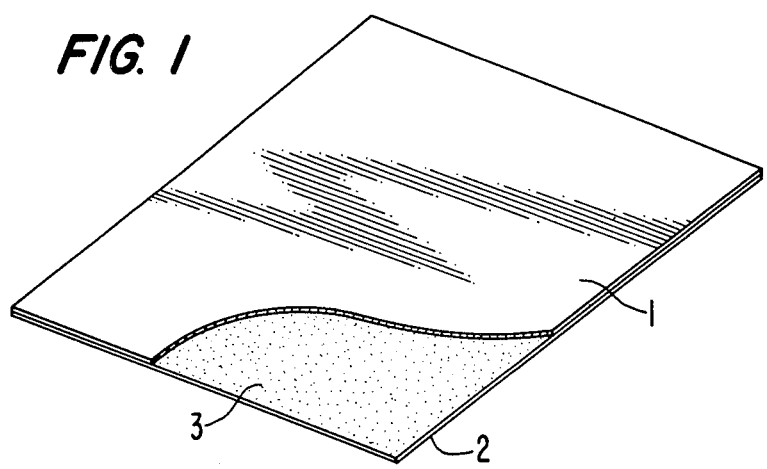
FIG. 1 is a partly cutaway perspective view of the sheetlike battery used in this invention.

DETAILED DESCRIPTION OF THE INVENTION:

At first, a preferably sheetlike battery to be used in the present invention shall be described with reference to FIG. 1. As disclosed in PCT/JP84/00100 according to the previous application of the present inventor, this battery is composed of a positive electrode 1 in the form of a sheet densely having carbon fibers or fine carbon particles, a negative electrode 2 of metal foil such as aluminum and zinc, and an electrolyte 3 interposed between the two electrodes and made of office paste containing starch as the main ingredient or the like paste. The sheet material of the positive electrode is preferably made of fibrous paper, and the negative electrode 2 is preferably made of aluminum foil. The battery thus constructed can be made as thin as 1 mm or less, has flexibility similar to cardboard or medium-thickness paper, can be cut into any desired size and shape by scissors, and has a voltage of about 0.8 to 1.2 V regardless of being a large or small size piece.

In a therapeutic means according to the first embodiment of the present invention, the battery formed as set forth above is cut into small battery pieces 4, and the positive side 1 of the small battery piece 4 is adhered to the sticky face of an adhesive film 5. The adhesive film 5 is larger than the battery piece 4, so that the peripheral portion of the adhesive film 5 can be adhered to any desired part of the human body. Preferably, the adhesive film 5 should be a water-impermeable plastic film.

Figure 2:
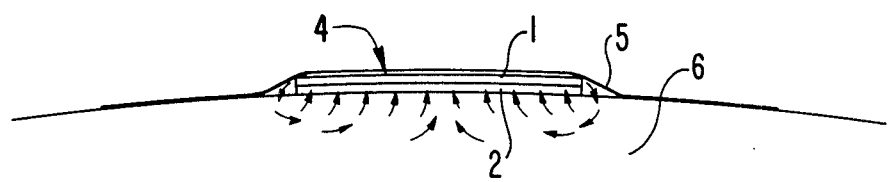
FIG. 2 to FIG. 4 are sectional views showing therapeutic means according to first to third embodiments of the present invention made from the sheetlike battery in FIG. 1 and attached to the skin of a human body.

To use the above-mentioned therapeutic means, the negative electrode side 2 of the small battery piece 4 is placed in contact with an affected part of the skin 6 of the human body, and the adhesive film 5 adhered to the positive electrode side 1 of the battery piece is attached to the skin surrounding the affected part. In such an arrangement, an electric circuit is formed for flowing a small amount of electric current, as shown by arrows in FIG. 2, from the positive electrode 1 of the battery to the negative electrode 2 thereof through the moisture on the inner surface of the adhesive film 5 and the tissues under the skin, thereby producing the therapeutic effects on the affected part as mentioned above (1), (2) and (3).

Figure 3:
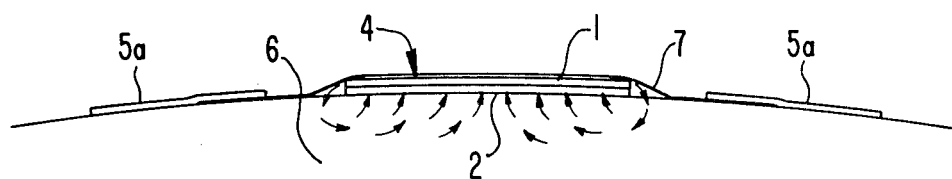

FIG. 3 shows a therapeutic means according to the second embodiment of the present invention, wherein the positive electrode side 1 of the small battery piece 4 is closely covered with a water-impermeable plastic film 7 larger than the battery piece 4, and an annular adhesive film 5a is adhered at the inner periphery thereof to the outer periphery of the plastic film 7, the outer periphery of the adhesive film 5a being used to attach this therapeutic means to the skin of the human body. When this therapeutic means is in use, an electric circuit is formed for flowing a small amount of electric current, as shown by arrows, from the positive electrode 1 of the small battery piece 4 to negative electrode 2 thereof through the moisture on the inner surface of the water-impermeable film 7 and the tissues under the skin, thereby producing the same therapeutic effects as in the first embodiment. In a modification of the second embodiment, the adhesive film 5a can be made large enough to entirely cover the water-impermeable film 7, so that the center portion of the adhesive film 52 is adhered to the entire upper surface of the water-impermeable film, and the peripheral portion of the adhesive film 52 is attached to the skin of the human body.

Figure 4:
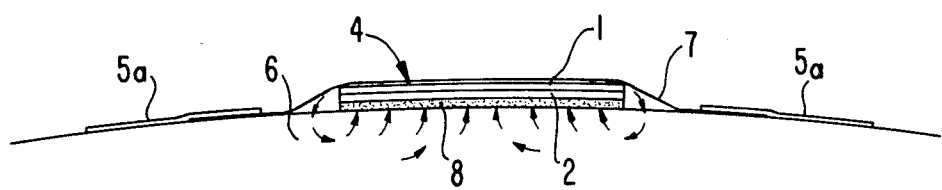

FIG. 4 shows therapeutic means according to a third embodiment of the present invention, wherein an absorbent sheet 8 is put on the negative electrode side of the small battery piece 4, so that the battery piece 4 is attached to the skin 6 by interposing the absorbent sheet piece 8 therebetween. The other construction of the third embodiment is the same as the second embodiment shown in FIG. 3. The absorbent sheet 8 of the therapeutic means in the third embodiment is employed to absorb the moisture since a relatively large amount of moisture permeates through the skin face, when the small battery piece 4 of the present invention is used as in the cases of the first and second embodiments. The absorbent sheet 8 may contain an antiseptic solution for skin wounds.

Figure 5:
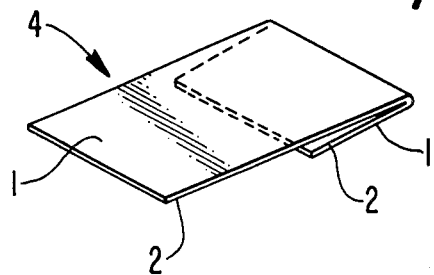
FIG. 5 is a perspective view of a battery to be used in further embodiments of the present invention, the battery being made by cutting the sheetlike battery in FIG. 1 into a small size and folding it.

In a therapeutic means according to a fourth embodiment of the present invention, the battery constructed as shown in Fig. 1 is cut into desired small pieces 4. Then, one side portion of the small battery piece 4 is folded (as shown in FIG. 5) in such a way that the positive electrode 1 and the negative electrode 2 are exposed side by side on the negative electrode side of the battery piece 4. An adhesive tape 5b is attached to the other positive side of the battery piece 4.

Figure 6:
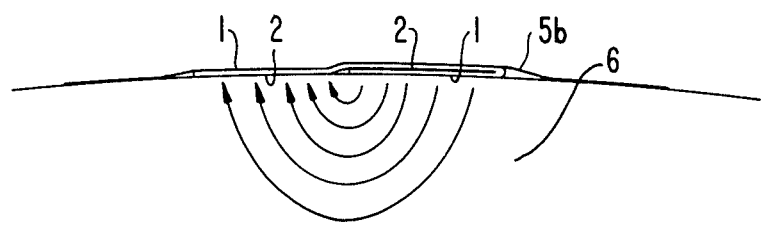
FIG. 6 to 8 are sectional views showing therapeutic means according to fourth to sixth embodiments of the present invention made from the sheetlike battery in FIG. 1 and attached to the skin of the human body.

When the therapeutic means of the fourth embodiment is used, the above-mentioned side of the small battery piece, where the positive and negative electrodes are exposed side by side, is placed in contact with an affected part of the human body, and the battery piece is adhered to the skin around the affected part of the adhesive tape 5b attached to the other side of the battery piece. In this case, preferably, the battery piece 4 is attached such that the negative electrode thereof be placed upon the affected part. In such an arrangement, an electric circuit is formed as shown by arrows in FIG. 6 to flow a small amount of electric current from the positive electrode 1 of the small battery piece 4 to the negative electrode 2 through the affected part of the skin 6, thereby producing the therapeutic effects as mentioned above in (1), (2) and (3).

Figure 7:
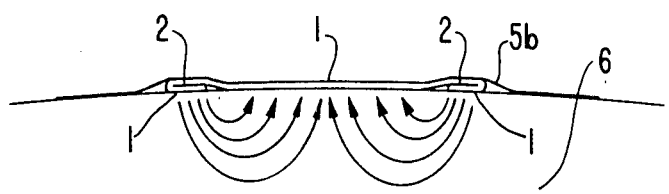

FIG. 7 shows a therapeutic means according to a fifth embodiment of the present invention, wherein the small battery piece 4 cut into a rectangular shape is folded at both edge portions, with the negative electrode inside, so that one side surface of the thus folded small battery piece 4 has positive electrodes 1 at both side edges and the negative electrode 2 at the center part. When in use, the negative electrode 2 of the above one side surface is placed in contact with the affected part and the small battery piece 4 is attached to the skin by the adhesive tape 5b adhered to the other side face of the battery. In the case of this embodiment, an electric circuit is formed, as shown by arrows, from the positive electrodes at both sides of the affected part to the negative electrode through the affected part, so that a small amount of electric current flows in the affected part from both sides thereof with the increased current density, thereby enhancing the therapeutic effects.

Figure 8:
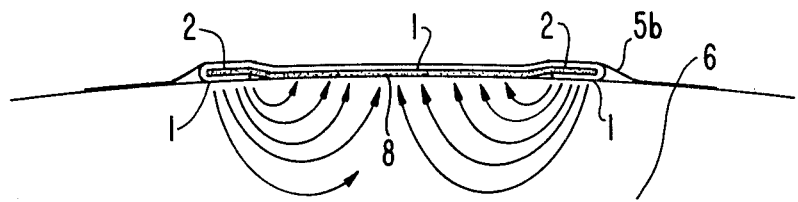

FIG. 8 shows a therapeutic means according to a sixth embodiment of the present invention, wherein an absorbent sheet 8, like gauze, is put on the central negative electrode face of the small battery piece 4 which is folded and formed as in the case of FIG. 4. The negative electrode side of the small battery piece 4 is placed on the affected part by interposing the absorbent sheet 8 therebetween. The other construction of this embodiment is the same as that of the fifth embodiment shown in FIG. 7. The absorbent sheet 8 of the therapeutic means according to the sixth embodiment is employed to absorb the moisture as in the case of the third embodiment, since a relatively large amount of moisture permeates through the skin part where the small battery piece 4 is attached.

In the embodiments set forth above, although it is disclosed that the small battery pieces be attached to the affected part of the skin 6 by adhesive film or adhesive tape 5, 5a, 5b, the small battery piece can be closely attached on the skin by means of a bandage in such an event that a wide piece of the battery 4 is used. In such case, the double layer construction of the present battery composed of the fibrous paper and the aluminum foil makes it possible to follow the curvature of the skin and to be closely attached thereto because of the extremely high flexibility.

As described above, according to the therapeutic method of the present invention, an electric circuit is formed to flow a small amount of electric current into an affected part of the human body from the positive electrode to the negative electrode through the affected part by placing the negative electrode of the flexible sheetlike battery in contact with the affected part, whereby unexpected therapeutic effects can be attained, such as relieving of muscular pain and stiff shoulders and curing athlete's foot, skin diseases and the like.

Further, the therapeutic means according to the present invention comprises a very thin sheetlike battery in order that the negative electrode thereof be placed in contact with an affected part, whereby the present therapeutic device can be attached at any time to the affected part by a covering member such as adhesive film, adhesive tape and bandage. Therefore, the present therapeutic means makes it possible to have continuous therapeutic effects with very easy application to the human body. Also, there is no feeling of physical discomfort, when the present therapeutic means is in use, because of the very thin structure thereof. Especially, in case the sheetlike battery is composed of a sheetlike positive electrode having dense carbon fibers or fine carbon particles therein, a negative electrode of metal foil such as aluminum foil or zinc foil, and an electrolyte interposed between the positive and negative electrodes, the sheetlike battery can be cut into a desired size with scissors and, thereafter, it can be folded to form the therapeutic means. In addition, the therapeutic means formed from such sheetlike battery has other remarkable advantages because of flexibility and extremely low cost.

I claim:

1. A therapeutic apparatus for treating an affected part of a human body, said apparatus comprising:
    a sheetlike battery including opposite surfaces defining positive and negative electrodes and having flexibility and cutting characteristics similar to paper;
    said sheetlike battery being cut to form a sheetlike battery piece of a size and shape for fitting over an affected body part to be treated; and
    means for attaching said battery piece to the affected body part and thereby for forming an electric, current-conducting circuit between said battery and skin of the affected body part by means of contact therewith of body moisture.

2. An apparatus as claimed in claim 1, wherein said sheetlike battery piece is folded such that portions of body said positive and negative electrodes are exposed on one side of the thus folded piece.

3. An apparatus as claimed in claim 2, wherein said sheetlike battery piece has a size in excess of the affected body part to be treated, and the excess size portion of said piece is folded.

4. An apparatus as claimed in claim 2, wherein said sheetlike battery piece is folded at opposite edges thereof, such that said one side exposes two opposite edge portions of one said electrode and a center portion of the other said electrode.

5. An apparatus as claimed in claim 4, further comprising a sheet of moisture absorbent material covering said center portion of said other electrode.

6. An apparatus as claimed in claim 2, further comprising a sheet of moisture absorbent material covering one of said exposed electrode portions on said one side of said folded piece.

7. An apparatus as claimed in claim 1, wherein said positive electrode comprises a sheet member densely containing carbon fibers or particles.

8. an apparatus as claimed in claim 1, wherein said negative electrode comprises a sheet member formed of metal foil.

9. An apparatus as claimed in claim 8, wherein said metal foil comprises aluminum foil or zinc foil.

10. An apparatus as claimed in claim 1, wherein said cut sheetlike battery piece is of a size equal to that of the affected body part to be treated.

11. An apparatus as claimed in claim 1, wherein said attaching means comprises a covering member of a size larger than that of said sheetlike battery piece, said covering member covering said sheetlike battery piece and having a periphery surrounding said sheetlike battery piece and attached to the skin of the body surrounding the affected body part to be treated.

12. An apparatus as claimed in claim 11, wherein said covering member is adhesive on one side thereof.

13. An apparatus as claimed in claim 11, wherein said covering member is moisture permeable.

14. An apparatus as claimed in claim 1, wherein said attaching means comprises adhesive tape.

15. An apparatus as claimed in claim 1, wherein said attaching means comprises a bandage.

16. An apparatus as claimed in claim 1, wherein said attaching means positions a first said electrode in direct contact with one part of the skin of the body and a second said electrode spaced from the skin, such that said electric circuit is formed between said electrodes by body moisture from another part of the skin of the body.

17. An apparatus as claimed in claim 1, wherein said attaching means positions said electrodes such that said electric circuit is formed therebetween by body moisture from one part of the skin of the body contacting a first said electrode and body moisture from another part of the skin of the body contacting a second said electrode.

18. An apparatus as claimed in claim 1, wherein said attaching position portions of both said electrodes in direct contact with parts of the skin of the body, thereby forming said electric circuit between said electrodes.

19. A method for treating an effected part of a human body, said method comprising:
   providing a sheetlike battery piece including opposite surfaces defining positive and negative electrodes and having flexibility and cutting characteristics similar to paper; and
   attaching said sheetlike battery piece to the affected body part and thereby forming an electric, current-conducting circuit between said battery and skin of the affected body part by means of contact therewith of body moisture, such that current generated by said circuit flows through the affected body part.

20. A method as claimed in claim 19, further comprising forming said sheetlike battery piece of a size and shape to fit over the affected body part, and said attaching comprises placing a first said electrode in electrical contact with the affected body part.

21. A method as claimed in claim 20, comprising placing said first electrode in direct contact with the affected body part.

22. A method as claimed in claim 20, comprising interposing a sheet of moisture absorbent material between said first electrode and the affected body part, and absorbing body moisture into said sheet.

23. A method as claimed in claim 20, wherein said attaching comprises covering said sheetlike battery piece with a covering member of a size larger than said sheetlike battery piece, with said covering member in contact with a second said electrode, and attaching a peripheral portion of said covering member to the skin of the body around the affected body part, thereby maintaining said first electrode directed toward the affected body part.

24. A method as claimed in claim 23, comprising entrapping body moisture within said covering member between said peripheral portion thereof and the periphery of said sheetlike battery piece.

25. A method as claimed in claim 19, wherein said sheetlike battery piece is of a size in excess of the size of the affected body part, and folding the excess size portion to thereby expose portions of both said positive and negative electrodes on the one side of the thus folded piece, and said attaching comprises placing one of the said exposed electrode portions in direct contact with the skin of the affected body part of said human body, and placing the other of said exposed electrode portions in contact with another part of the skin of the body adjacent to the affected body part.

26. A method as claimed in claim 25, comprising folding at least two opposite edge portions of said excess size portion of said sheetlike battery piece, thereby exposing two opposite edge portions of a first said electrode and a center portion of a second said electrode, placing said center portion of said second electrode in electrical contact with the skin of the affected body part, and placing said two folded exposed edge portions of said first electrode in direct contact with other parts of the skin of the body adjacent the affected body part.

27. A method as claimed in claim 26, further comprising interposing a sheet of moisture absorbent material between said center portion of said second electrode and the body part, and absorbing body moisture into said sheet.

* * * * *